(12) United States Patent
Snyder et al.

(10) Patent No.: US 9,310,516 B2
(45) Date of Patent: Apr. 12, 2016

(54) QUANTUM DOT-BASED IDENTIFICATION, LOCATION AND MARKING

(71) Applicant: Raytheon Company, Waltham, MA (US)

(72) Inventors: Jeffrey R. Snyder, Indianapolis, IN (US); Joshua D. Stokes, Ortonville, MI (US)

(73) Assignee: RAYTHEON COMPANY, Waltham, MA (US)

( * ) Notice: Subject to any disclaimer, the term of this patent is extended or adjusted under 35 U.S.C. 154(b) by 102 days.

(21) Appl. No.: 14/150,966

(22) Filed: Jan. 9, 2014

(65) Prior Publication Data

US 2015/0192693 A1    Jul. 9, 2015

(51) Int. Cl.
*G01N 21/64*    (2006.01)
*G01V 15/00*    (2006.01)
*G01V 8/12*    (2006.01)

(52) U.S. Cl.
CPC ...... *G01V 15/00* (2013.01); *G01V 8/12* (2013.01); *Y10S 977/95* (2013.01)

(58) Field of Classification Search
CPC .................................................... G01V 15/00
See application file for complete search history.

(56) References Cited

U.S. PATENT DOCUMENTS

| | | | | |
|---|---|---|---|---|
| 5,347,910 | A * | 9/1994 | Avila et al. | 89/41.22 |
| 6,450,816 | B1 * | 9/2002 | Gerber | 434/11 |
| 6,528,317 | B1 * | 3/2003 | Moss et al. | 436/56 |
| 7,975,615 | B1 * | 7/2011 | Apple | 102/512 |
| 8,651,390 | B2 * | 2/2014 | Hinch et al. | 235/494 |
| 2011/0226954 | A1 * | 9/2011 | Hinch et al. | 250/341.1 |

* cited by examiner

*Primary Examiner* — David Porta
*Assistant Examiner* — Edwin Gunberg
(74) *Attorney, Agent, or Firm* — Cantor Colburn LLP

(57) ABSTRACT

An identification system includes a quantum dot form factor disposed on an article, and quantum dots disposed on the quantum dot form factor, the quantum dots emitting a predetermined emission. A marking system includes a secondary reservoir including a plurality of quantum dots configured to be expelled from the reservoir and a means for dispersing the quantum dots from the secondary reservoir to engage the area to be marked. A location system includes a main reservoir having a plurality of quantum dots disposed within the main reservoir, wherein the main reservoir is a water dissolvable material that dissolves over a predetermined period while exposed to water. An identification system includes a sensor for detecting a light wave query, a strobe for flashing, and a filter that includes quantum dots that the light from the strobe energizes to emit light at a predetermined frequency.

24 Claims, 8 Drawing Sheets

QUANTUM DOT-BASED IDENTIFICATION, LOCATION AND MARKING

BACKGROUND

The present invention relates to quantum dots, and more specifically, to systems and methods for quantum dot implementations for identification, location and marking.

There are currently various situations, for example in search and recovery missions and military missions, in which identification, location and marking are vital parts for the success of the mission. For example, in the military, friendly fire accidents are all too common due to poor means of identifying friendly troops and resources. Currently, crude marking systems, simple communication systems and tracking systems are implemented in an effort to avoid friendly fire accidents. However, in the heat of battle it is difficult to determine who is friendly and who is not. This is especially true when multiple countries and differing troop insignia are involved. Using colors for visual identification can be flawed because the ability of an individual to see the colors is needed, which may not be the case. In addition, the ability to see colors at night may be severely compromised. Communication systems can take too much time to implement and can also be flawed, due to the possibility of multiple languages and communication systems between allied countries. Although computerized tracking systems are by far the most effective, they are expensive to implement across all platforms.

In another example, a military needs to mark enemy positions, without detection, during both the day and night. Typically, smoke canisters are used to mark the enemy positions. However, smoke is difficult to see at night, which is typically the time in which many military operations are performed. In addition, smoke can be seen by everyone including the enemy.

In still another example, in search and rescue operations, both civilian and military, search times for aircraft crash and sinking boat survivors in large bodies of water can be excessive. Radio beacons require maintenance and need to be activated manually. In addition, radio beacons are expensive, and so there is typically only one per vehicle (not per passenger). It can be difficult to find aircraft (especially small aircraft) that have gone down in large bodies of water. It is also difficult to find ships/boats, especially small ones, which have sunk. Therefore, rescue attempts may involve searching large areas. Radio beacon batteries may not be maintained causing them not to work or not to work long enough. If the radio beacon sinks with the aircraft or boat it can no longer be detected. In addition, most beacons must be manually activated. This may not be feasible (especially with aircraft). The radio beacons also fail to provide a visible marker for the rescuer. As described above, the radio beacons typically mark the location of the aircraft or boat. Since individual survivors may not be in proximity of the aircraft or boat, it can be difficult to find the individual survivors.

SUMMARY

Exemplary embodiments include an identification system for identifying an article, including a quantum dot form factor disposed on the article, and a plurality of quantum dots disposed on the quantum dot form factor, the plurality of quantum dots configured to emit a predetermined emission for detection by an external receiver.

Additional exemplary embodiments include a marking system, including a secondary reservoir including a plurality of quantum dots configured to be expelled from the reservoir and a means for dispersing the quantum dots from the secondary reservoir to engage the area to be marked.

Additional exemplary embodiments include a location system, including a main reservoir having a plurality of quantum dots disposed within the main reservoir, wherein the main reservoir is a water dissolvable material that dissolves over a predetermined period while exposed to water.

Further exemplary embodiments include an identification system for allowing a person or thing to identify themselves by emitting a coded light frequency in response to a light wave query, the identification system including a sensor for detecting a light wave query, a strobe for flashing in response to the detection of a light wave query, and a filter at least partially covering said strobe, said filter including quantum dots that the light from the strobe energizes to emit light at a predetermined frequency which may be detected to determine the identity of the person or thing.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
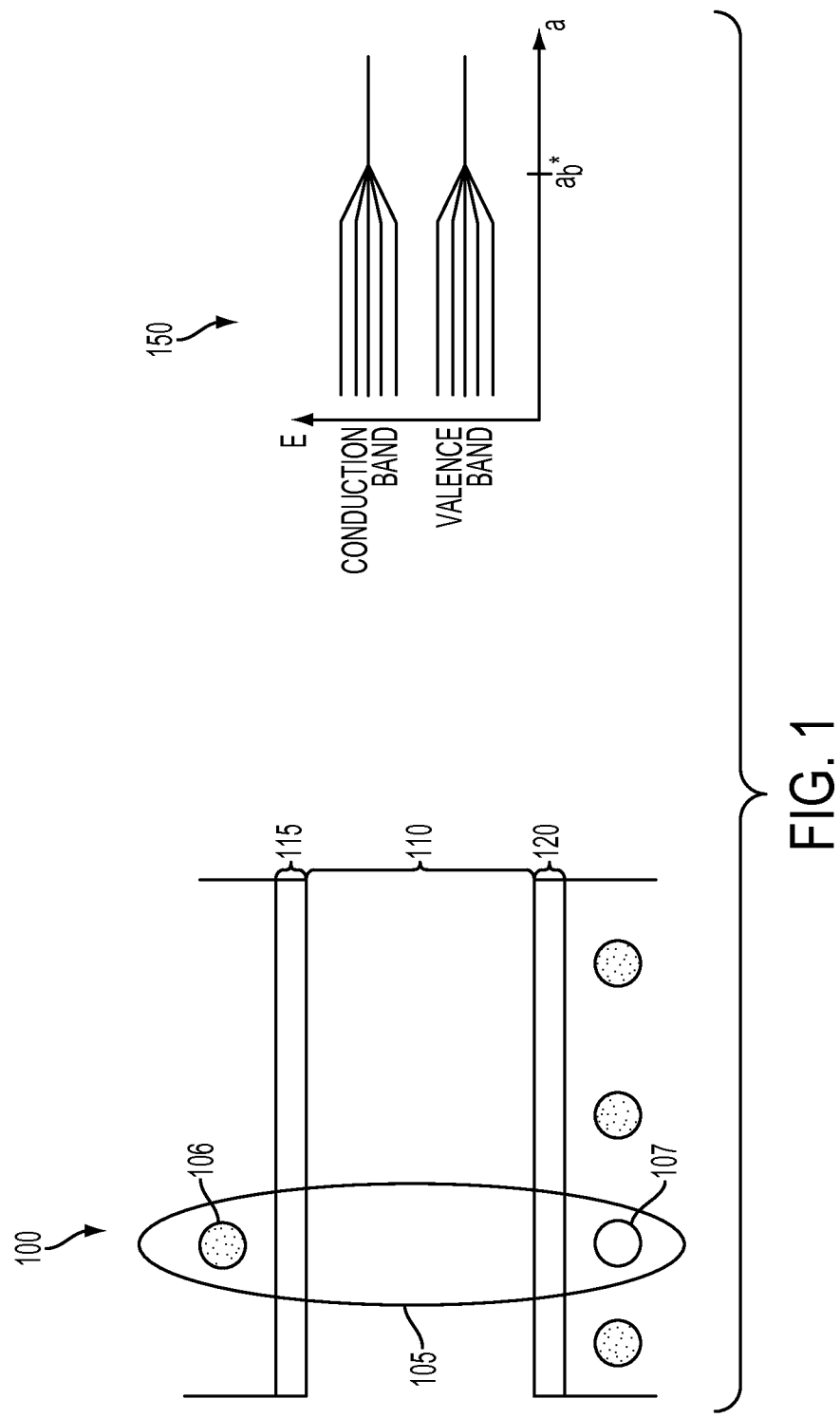
FIG. 1 illustrates an example of an energy diagram illustrating the energy levels of a quantum dot.

In exemplary embodiments, the systems and methods described herein implement quantum dots in order to carry out various identification, location and marking operations, both in civilian and military operations. Although the description herein discusses a few examples of identification, location and marking operations, it will be appreciated that other operations are contemplated in other exemplary embodiments.

A quantum dot can be in various form factors, and it will be appreciated that the quantum dots described herein can be in various form factors. Quantum dots of different sizes can be assembled into a gradient multi-layer nanofilm. A quantum dot is a portion of matter (e.g., a semiconductor) whose excitons are confined in all three spatial dimensions. Consequently, such materials have electronic properties intermediate between those of bulk semiconductors and those of discrete molecules. As such, they have the advantage of displaying properties of both bulk material and individual molecules. A quantum dot can be easily viewed as a semiconductor whose electronic characteristics are closely related to the size and shape of the individual crystal. Generally, the smaller the size of the crystal, the larger the band gap, the greater the difference in energy between the highest valence band and the lowest conduction band becomes. Therefore, more energy is needed to excite the dot, and concurrently, more energy is released when the crystal returns to its resting state. For example, in fluorescent dye applications, this equates to higher frequencies of light emitted after excitation of the dot as the crystal size grows smaller, resulting in a color shift from red to blue in the light emitted. In addition to such tuning, a main advantage with quantum dots is that, because of the high level of control possible over the size of the crystals produced, it is possible to have very precise control over the conductive properties of the material.

In a semiconductor crystal lattice, the electrons are squeezed together, since no two nearby electrons can share exactly the same energy level according to the Pauli Exclusion Principle, leading to quantum confinement. The energy level can then be modeled using particle in a box, which leads to the conclusion that the energy levels of the quantum dot are dependent on its size. When the size of the quantum dot is smaller than the critical characteristic length called the Exciton Bohr radius, the electrons crowding lead to the splitting of the original energy levels into smaller ones with smaller gaps between each successive level. The Exciton Bohr radius is larger than the Bohr radius due to the effect of dielectric screening and the influence of periodic lattice structure of the crystal. The quantum dots that have radii larger than the Exciton Bohr radius are said to be in the 'weak confinement regime' and the ones that have radii smaller than the Exciton Bohr radius are said to be in the 'strong confinement regime'. Thus, if the size of the quantum dot is small enough that the quantum confinement effects dominate (e.g., less than 10 nm), the electronic and optical properties change, and the fluorescent wavelength is determined by the size.

Splitting of energy levels for small quantum dots due to the quantum confinement effect. The horizontal axis is the radius, or the size, of the quantum dots and $a_b^*$ is the Exciton Bohr radius.

The fluorescence of the quantum dots is a result of exciting the valence electron with a certain energy (or wavelength) and the emission of lower energy in the form of photons as the excited electron returns to the ground state, combining with the hole. The energy of the emitted photon is determined by the size of the quantum dot due to quantum confinement effects. In a simplified model of the excitation, the energy of the emitted photon can be seen as a sum of the band gap energy between occupied level and unoccupied energy level, the confinement energies of the hole and the excited electron, and the bound energy of the exciton (the electron-hole pair).

FIG. 1 illustrates an example of an energy diagram illustrating the energy levels of a quantum dot. The energy diagram 100 includes an exciton 105 (electron-hole pair between an electron 106 and a hole 107), a band gap 110, confinement energy 115 of the excited electron 106, and confinement energy 120 of the hole 107. FIG. 1 further illustrates an energy versus distance plot 150 of the energy diagram 100. The band gap 110 can become smaller in the strong confinement regime where the size of the quantum dot is smaller than the Exciton Bohr radius, $a_b^*$, as the energy levels split up, where $a_b$ is the Bohr radius=0.053 nm, m is the mass, μ is the reduced mass, and $\in_r$ is the size-dependent dielectric constant. As such, there is an increase in the total emission energy (i.e., the sum of the energy levels in the smaller band gaps in the strong confinement regime is larger than the energy levels in the band gaps of the original levels in the weak confinement regime) and the emission at various wavelengths. A similar effect occurs in the sun, where the quantum confinement effects are completely dominant and the energy levels split up to the degree that the energy spectrum is almost continuous, thus emitting white light.

With respect to confinement energy 115 of the electron 106, the exciton 105 entity can be modeled using the particle in the box. The electron and the hole can be seen as hydrogen in the Bohr model with the hydrogen nucleus replaced by the hole of positive charge and negative electron mass. Then the energy levels of the exciton can be represented as the solution to the particle in a box at the ground level (n=1) with the mass replaced by the reduced mass. Thus, by varying the size of the quantum dot, the confinement energy of the exciton can be controlled.

With respect to the bound exciton energy 120 of the hole 107, there is Coulomb attraction between the negatively charged electron 106 and the positively charged hole 107. The negative energy involved in the attraction is proportional to Rydberg's energy and inversely proportional to square of the size-dependent dielectric constant of the semiconductor. When the size of the semiconductor crystal is smaller than the Exciton Bohr radius, the Coulomb interaction must be modified to fit the situation.

Therefore, the sum of these energies can be represented as:

$$E_{confinemnet} = \frac{\hbar^2 \pi^2}{2a^2}\left(\frac{1}{m_e} + \frac{1}{m_h}\right) = \frac{\hbar^2 \pi^2}{2\mu a^2}$$

$$E_{exciton} = -\frac{1}{\epsilon_r^2}\frac{\mu}{m_e}R_y = -R_y^*$$

$$E = E_{bandgap} + E_{confinement} + E_{exciton}$$

$$= E_{bandgap} + \frac{\hbar^2 \pi^2}{2\mu a^2} - R_y^*$$

where:
μ is the reduced mass
a is the radius
$m_e$ is the free electron mass
$m_h$ is the hole mass
$\in_r$ is the size-dependent dielectric constant
In addition, the relationship between $$a_b^* = \varepsilon_r\left(\frac{m}{\mu}\right)a_b$$

Although the above equations are derived using simplifying assumptions, the energy of the quantum dots are dependent on their size due to the quantum confinement effects, which dominate below the critical size leading to changes in the optical properties. This effect of quantum confinement on the quantum dots have been experimentally verified and are key features of the systems and methods described herein.

It will also be appreciated that in other exemplary embodiments, structures having confinement other than in all three dimensions (i.e., a quantum dot), other quantum confined semiconductors include: quantum wires, which confine electrons or holes in two spatial dimensions and allow free propagation in the third; and quantum wells, which confine electrons or holes in one dimension and allow free propagation in two dimensions.

Figure 2A:
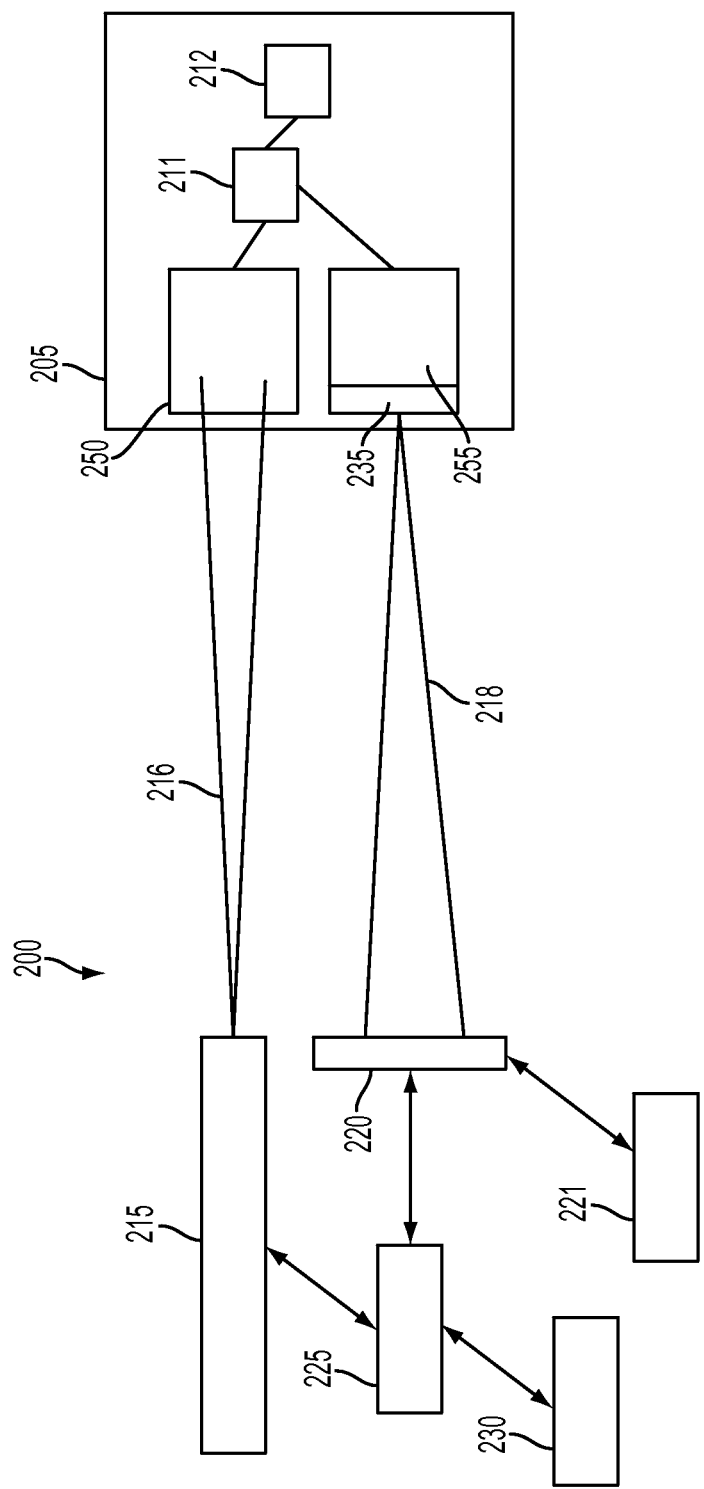
FIG. 2A illustrates a system level diagram of an exemplary active friendly fire prevention system.

In exemplary embodiments, the systems and methods described herein can be implemented to prevent friendly fire accidents as now described. In exemplary embodiments, quantum dots with prescribed emission (spectrum) bands can be implemented to provide a system and method for identifying friendly soldiers and equipment. FIG. 2A illustrates a system level diagram of an exemplary active friendly fire prevention system 200. The system 200 includes an article 205, which broadly represents a friendly person or object. The system 200 further includes a wave source 215 (e.g., an ultraviolet (UV) laser) that is implemented to activate a sensor 250 on the article 205. The system 200 further includes a receiver 220 that interprets the wavelengths of the incident light to determine if a friendly force is in the line of fire. In exemplary embodiments, an incident beam 216 from the wave source 215 can be shined on the sensor 250 the triggers a strobe 255 that generates a flash 218, which is detected by the receiver 220 as further described herein. If a friendly force is in the line of fire the unit (e.g., from the receiver 220) will provide a signal to the operator or to a weapon system as a lockout.

FIG. 2A illustrates a generalized device 221 that can represent a weapon, weapon system or other system that can communicate a disabling signal as described herein. It can be appreciated that the system 200 can be affixed on any weapon or weapon system. The system can be activated, constantly emitting the incident beam and immediately recognizing friendly articles, or the system 200 can be operated manually, emitting the incident beam 216 when needed, or a combination of both. It can be appreciated that the system 200 takes the guesswork out of determining if a target (i.e., article 205) is friendly, and that friend or foe can be determined in an instant with very little hardware. With targeting systems, the system 200 can either provide a response to the operator and/or send a lockout code to the weapon being used. In exemplary embodiments, although visible spectrum is contemplated, by using frequencies outside of the visible spectrum it would be undetectable to the naked eye (reducing enemy detection). The system 200 can include a self-contained power source 225. It can further be appreciated that the system can easily be changed to adapt to the changing environment. (i.e., if some vehicles are captured the patches/filters/tape can be changed so the enemy will actually give away their positions by having the wrong identification). In exemplary embodiments, the system 200 is a high visibility solution that still provides concealment from enemy forces. It can be implemented very quickly and is capable of being used on all platforms including the individual soldiers.

In exemplary embodiments, the system 200 system 200 can include a small flexible and durable solar panel 230. The solar panel 230 can be used to charge the battery 225 as well as a sensor to control triggering as further described herein. The wave source 215 emits the incident beam 216 as described herein, which can be in a hemispherical shape. As described herein, the wave source 215 can be part of a weapon system. A sensor 250 would detect the incident beam 216 from the wave source 215 (and weapon system). Sensing the incident beam 216 triggers a strobe 255 (e.g., a wave source on the article 205) to emit the flash 218. The strobe 255 would be covered with a filter 235. In exemplary embodiments, the filter 235 includes quantum dots, allowing the filter 235 to be tunable. As such, the filter 235 can be made using quantum dots to emit in a single or multiple frequency bands. By tuning the emitted frequencies with filters, the system 200 can easily be changed (periodically) to prevent enemies from using captured or stolen devices as a "Trojan horse". As long as all of the frequencies used are in the UV spectrum (for example) they cannot be seen with the naked eye (or even night vision). Thereby keeping the location of friendly fire concealed to the enemy. In this way, the filter 235 can be implemented to generate a coded identification. The emitted beam 216 and the flash form the strobe 235 can be in the UV spectrum so the naked eye cannot detect it (prevents giving away position to the enemy). As described herein, quantum dots are able to be excited using a wide range of frequencies. However, due to the quantum effect, they only emit in a single frequency. Current production methods are able to produce quantum dots of remarkably consistent sizes. The size controls the emitted frequency. A controlled mixture of multiple dot sizes would essentially produce a coded emission. The emitted flash 218 from the strobe 255 (after illuminating and passing through the filter 235) would be a tuned emission. Then the sensor 220 on the weapon system would receive the emission from article 205 and determine friend or foe. The active option can be powered by a solar panel 230 and battery 225 or other suitable power supply. The emitted flash 218 from the strobe 255 (through the filter 235) on article 205 can be in a hemispherical pattern since the direction of the incident beam (from the weapon system aimed at it) is unknown. The sensor 250 and strobe 255 can have its own power source 211 and solar panel 212.

In addition to the quantum dot filter 235, a quantum dot based triggering mechanism can be implemented. The triggering device would be activated by being exposed to a significant concentration of UV light. In this way, the solar panel 230 can have a dual purpose. Since the sun emits UV light, the intensity of the sunlight can be determined from the solar panel and used to adjust the required emission of light from the quantum dots to trigger the device. The light emitted from the quantum dots for triggering would be in the visible range so they can activate a photodiode that is protected by a window. The close proximity of the dots to the diode would require a very small amount of light that would be unlikely to be detected by the human eye.

In exemplary embodiments, weapons from friendly forces would need to be adapted with a UV laser that could "illuminate" the article 205 just prior to firing. When one of the UV strobes is illuminated with a UV laser it will "fire" (i.e., emit a flash of UV light). The weapon mounted system would then detect the high intensity UV light from the target. The weapon can then be locked out (will not fire) or a warning can be displayed or a lockout with secondary override can be used. In any case, the chance of having a friendly fire casualty is greatly reduced.

Figure 2B:
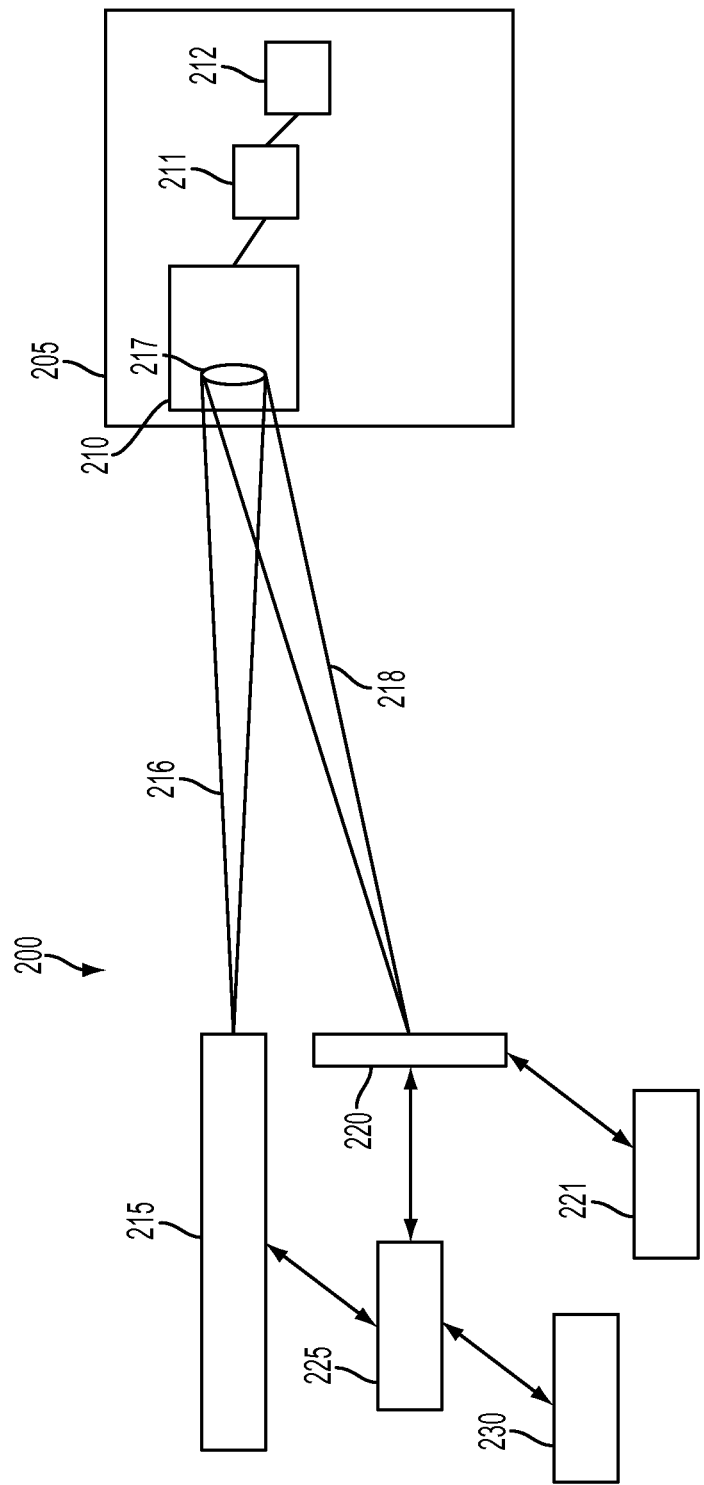
FIG. 2B illustrates a system level diagram of an exemplary passive friendly fire prevention system.

FIG. 2B illustrates a system level diagram of an exemplary passive friendly fire prevention system 200. The system 200 includes an article 205, which broadly represents a friendly person or object. The article 205 includes a quantum dot form factor 210 which can include an array or other arrangement of quantum dots. The system 200 further includes a wave source 215 (e.g., an ultraviolet (UV) laser) that is implemented to activate the quantum dots on the quantum dot form factor 210. The system 200 further includes a receiver 220 that interprets the wavelengths of the incident light to determine if a friendly force is in the line of fire. In exemplary embodiments, an incident beam 216 from the wave source 215 can be shined on the quantum dot form factor 210, generated an area of excitation 217, resulting in a excited beam signal 218, which is detected by the receiver 220. If a friendly force is in the line of fire the unit (e.g., from the receiver 220) will provide a signal to the operator or to a weapon system as a lockout.

FIG. 2B illustrates a generalized device 221 that can represent a weapon, weapon system or other system that can communicate a disabling signal as described herein. It can be appreciated that the system 200 can be affixed on any weapon or weapon system. The system can be activated, constantly emitting the incident beam and immediately recognizing friendly articles, or the system 200 can be operated manually, emitting the incident beam 216 when needed, or a combination of both. It can be appreciated that the system 200 takes the guesswork out of determining if a target (i.e., article 205) is friendly, and that friend or foe can be determined in an instant with very little hardware. With targeting systems, the system 200 can either provide a response to the operator and/or send a lockout code to the weapon being used. In exemplary embodiments, although visible spectrum is contemplated, by using frequencies outside of the visible spectrum it would be undetectable to the naked eye (reducing enemy detection). The system 200 can include a self-contained power source 225. It can further be appreciated that the system can easily be changed to adapt to the changing environment. (i.e., if some vehicles are captured the patches/filters/tape can be changed so the enemy will actually give away their positions by having the wrong identification).

In the passive option, the article 205 includes the quantum dot form factor 210. When the dots are illuminated with a UV laser from the weapon, they will emit in their respective wavelengths. This method may not be as effective, since emission from the patches would be directly proportional to the intensity of incident UV light. The passive options implement the same quantum dots as the active option but do not use a powered strobe to activate the quantum dots. The quantum dots are energized by an external energy source such as a laser, sunlight, headlight (from a vehicle), such as from the wave source. Currently, reflective tape is used in theatre to mark vehicles. Some spell out the radio frequency that they are using on the side of their turret. When approaching other vehicles they turn their turret sideways to show their frequency such that if the oncoming vehicle is friendly they can contact them directly. In exemplary embodiments, when the quantum dots are energized they will emit in their respective frequencies. The same laser and "coded" identification receiver can be used for all three systems.

In exemplary embodiments, the quantum dot form factor 210 can also be an active form factor, having its own power source 211 and solar panel 212. In this way, the article can be constantly emitting quantum dot emissions similar to the active options described herein, enabling the receiver 220 to pick up the emissions, having the same friendly fire prevention results described herein.

Figure 3:
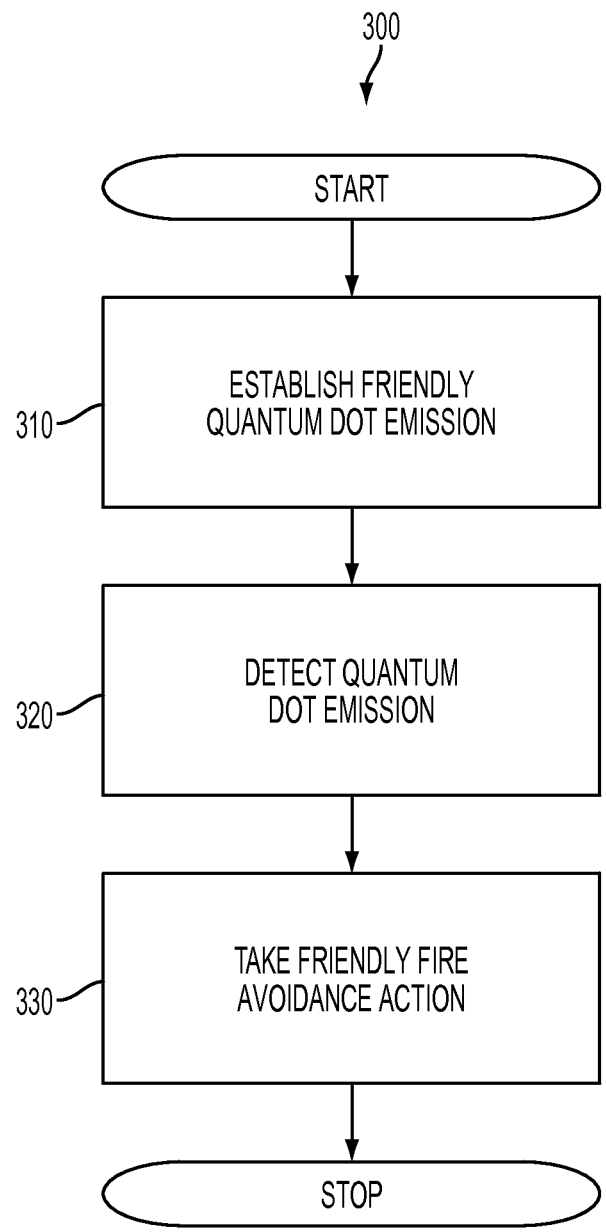
FIG. 3 illustrates a flow chart of a method for preventing friendly fire accidents implementing quantum dots in accordance with exemplary embodiments.

Regardless of the active or passive options, the methodology implemented is similar. FIG. 3 illustrates a flow chart of a method 300 for preventing friendly fire accidents implementing quantum dots in accordance with exemplary embodiments. At block 310, a quantum dot emission spectrum is selected, which indicates a friendly article. As such, regardless of the passive or active detection methods implemented, a pre-selected emission is known, which, when detected at block 320, indicates a friendly target. At block 330, actions can then be taken to avoid a friendly fire accident. For example, as described herein, the weapon or weapon system coupled to the system 200 can be disabled.

In exemplary embodiments, the systems and methods described herein can also be implemented for identifying positions during both day and night operations. As described herein, quantum dots with prescribed emission bands can be implemented to locate positions as well.

Marking positions with smoke grenades has been done for many years. While the purpose is to provide a visual aid for targeting, extraction or aid, the visual aid is seen by both sides. Therefore, the enemy forces take action to mitigate the effectiveness of the smoke/marker. In exemplary embodiments, the systems and methods described herein produce a high visibility marker that also provides concealment from enemy forces. It can be integrated easily by simply replacing typical smoke canisters with the proposed device (form, fit and enhanced function replacement).

Figure 4:
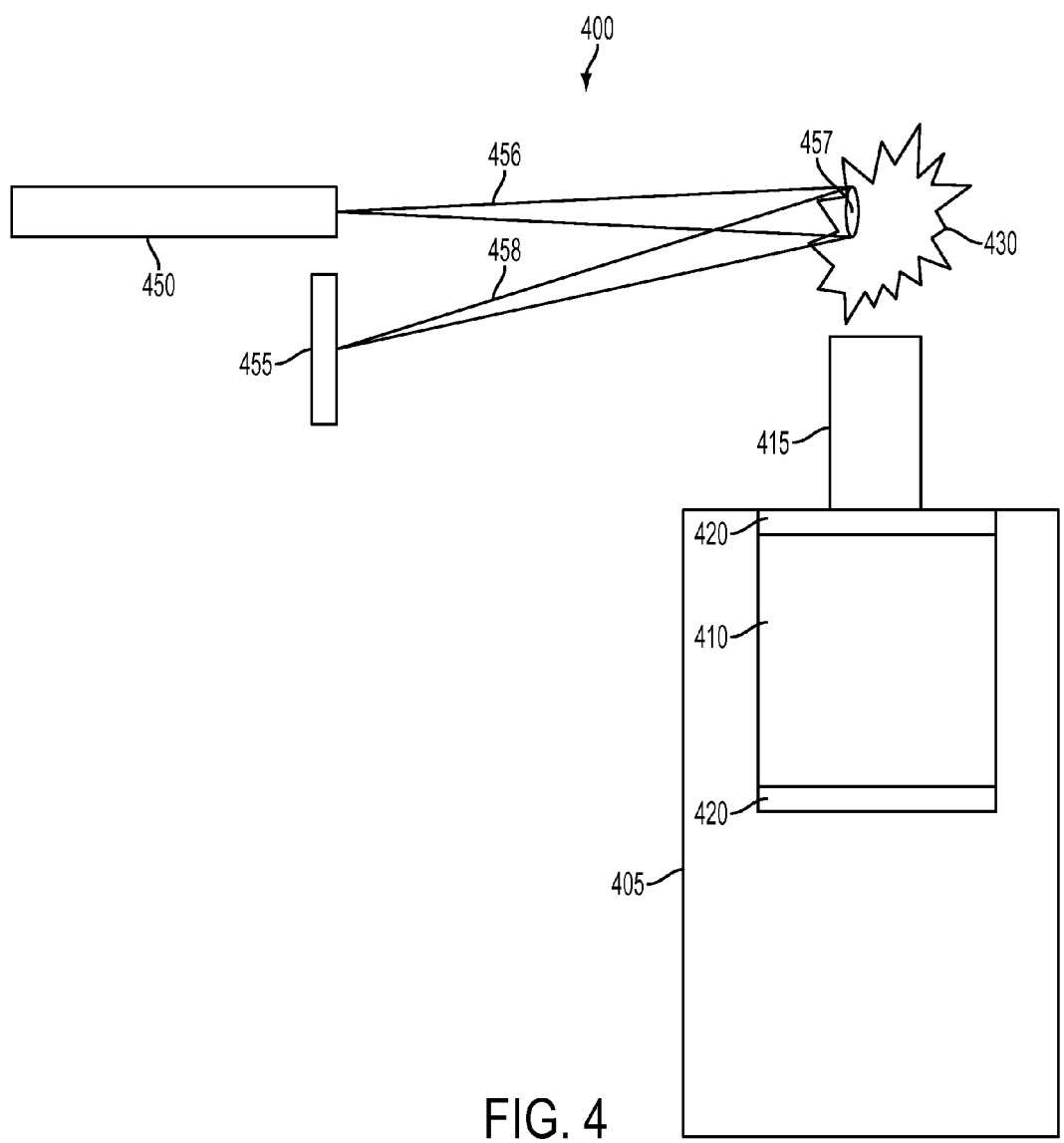
FIG. 4 illustrates an exemplary marking device.

In exemplary embodiments, a quantum dot marker device can be many form factors including, but not limited to, a canister filled with a compressed gas and a dispersible powder containing quantum dots. FIG. 4 illustrates an exemplary marking device 400. As described herein, the device 400can be a canister having a main reservoir 405, which can include a compressed gas such as an aerosol. A secondary reservoir 410 can be disposed within the main reservoir 405, and can include quantum dots and optionally an additional dispersant, which can couple with the quantum dots for easier dispersing of the quantum dots into a cloud. The device 400 can further include a trigger 415 coupled to the main reservoir 405 and the secondary reservoir. Thin breakable membranes 420 can isolate the compressed gas in the main reservoir 405 and the quantum dots (and dispersant) within the secondary reservoir 410. Once the trigger 415 is activated (e.g., manually, with a detonator and the like) the pressure of the compressed gas within the main reservoir 405 can break through the membranes 420, and therefore expelling the quantum dots (and the dispersant) into the environment external to the device 400. In this way, a quantum dot cloud 430 similar to conventional smoke canisters is generated. However, as described herein, the resulting quantum dot cloud is either barely visible or invisible to the naked eye. In exemplary embodiments, a wave source 450 (e.g., a UV laser) can be implemented to activate the quantum dots in the quantum dot cloud 430. A receiver 455 that interprets the wavelengths of the incident light to determine the presence of the strategically placed device 400. In exemplary embodiments, an incident beam 456 from the wave source 450 can be shined into the quantum dot cloud 430, generating an area of excitation 457, resulting in a excited beam signal 458, which is detected by the receiver 455.

In exemplary embodiments, the quantum dots in the quantum dot cloud 430 can be of a predetermined size(s) to produce predetermined light frequency emissions when excited. When the device 400 is activated, the gas charge is released with the powder. As described herein, the resulting quantum dot cloud 430 would not necessarily be visible to the naked eye. When the cloud is illuminated by the wave source 450, the quantum dots absorb the incident light and emit in their respective frequencies. The quantum dot cloud 430 is then visible using the receiver 455 that can process the frequencies given off by the quantum dots.

It can be appreciated that the detection of the emissions from the quantum dot cloud 430 is different than shining a light on a cloud of smoke. In the case of smoke, the light still remains somewhat directional. In exemplary embodiments, the wave source 450 shining on the quantum dot cloud 430 (directionally) is absorbed and reemitted at random. Any light reemitted at a point inside the quantum dot cloud 430 is likely reabsorbed and reemitted as it reaches the outer edges. The absorption and reemission produces a glowing quantum dot cloud 430 rather than smoke with a light shining through it with some light scattering. It may also be undetectable to the naked eye depending on density.

Figure 5:
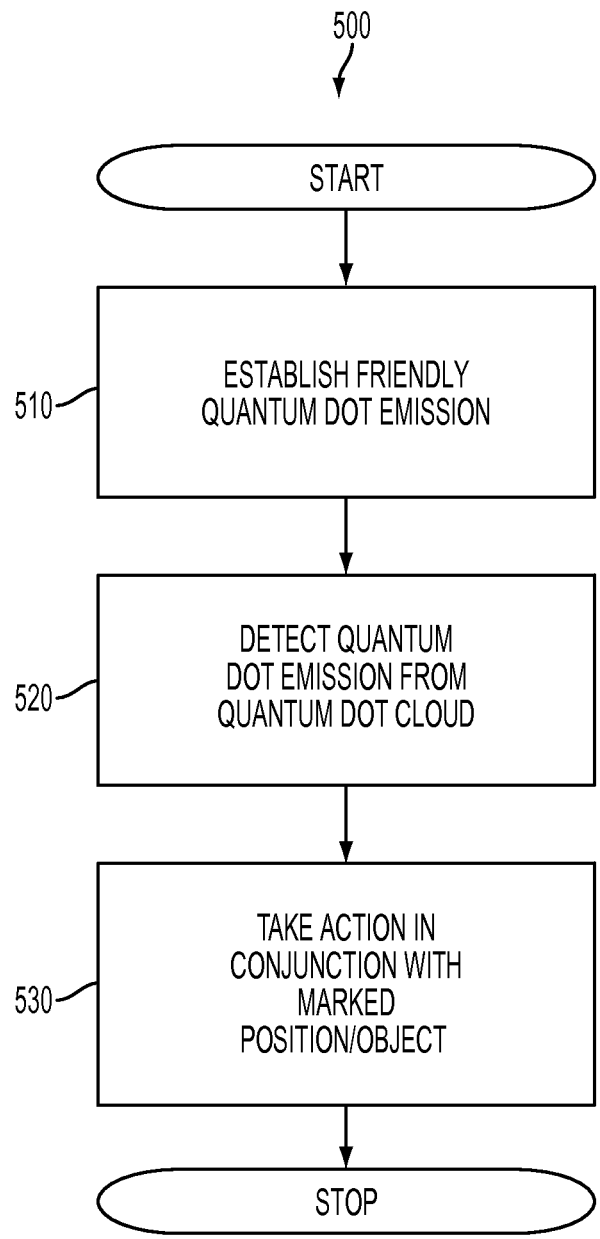
FIG. 5 illustrates a flow chart of a method for marking positions/objects implementing quantum dots in accordance with exemplary embodiments.

FIG. 5 illustrates a flow chart of a method 500 for marking positions/objects implementing quantum dots in accordance with exemplary embodiments. At block 510, a quantum dot emission spectrum is selected for marking positions/objects. As such, a pre-selected emission is known, which, when detected at block 520, upon activation of the device 400. At block 530, actions can then be taken in conjunction with the marked position/object.

In exemplary embodiments, the systems and methods described herein can also be implemented for locating aircrafts, boats or other objects in search, recovery and rescue operations. As described herein, quantum dots with pre-scribed emission bands that are uncommon in aquatic environments can be implemented in a method of locating victims of aircraft that have crashed in large bodies of water or of sinking/sunken boats.

In exemplary embodiments, the systems and methods described herein can implement quantum dots suspended in a material that is contained in a flotation device or a container attached to a flotation device, located at pre-determined positions within an aircraft or boat. The flotation device or container as described herein can be composed of a suitable material that when exposed to water dissolves over a period of time. Once the material has dissolved, the material in which the quantum dots are disposed is then dispersed into the water, and float on the surface of the water. The quantum dots are tuned to emit light in a specific frequency that is uncommon in aquatic environments (to prevent false readings). Then, high altitude aircraft or even satellites can scan the surface for that light frequency. Large areas can be scanned in a relatively short period of time.

Figure 6:
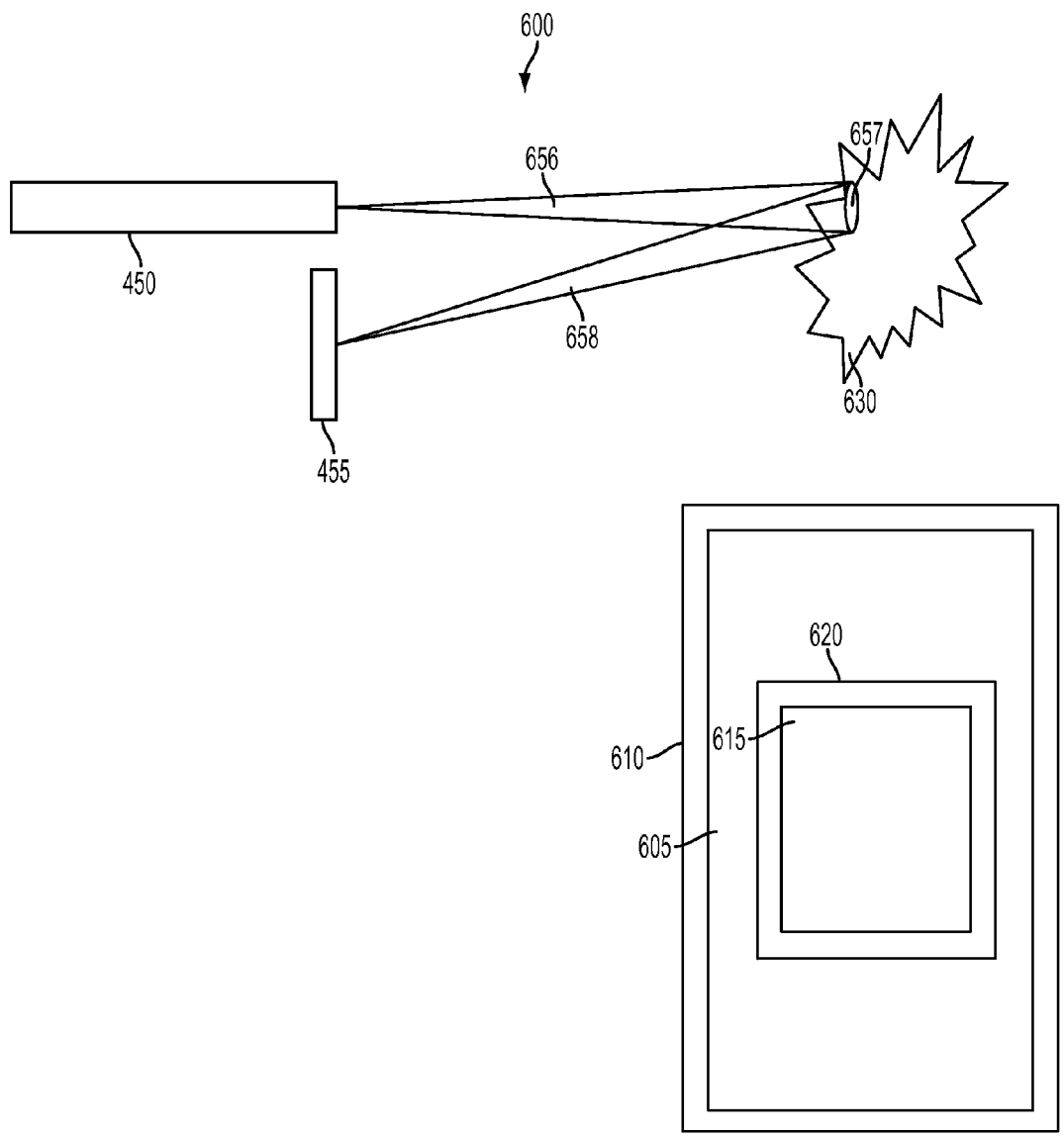
FIG. 6 illustrates an exemplary locating device.

In exemplary embodiments, a quantum dot locating device can be many form factors including, but not limited to, a canister filled with a material of density less than water, and dispersed with quantum dots, which also have a density less than water. FIG. 6 illustrates an exemplary locating device 600. As described herein, the device 600 can be a canister having a main reservoir 605, which can include a material with a density less than water and quantum dots. The main reservoir 605 can be made of a water dissolvable membrane 610, such that when dissolved, empties the inner material and quantum dots into the surrounding water environment. The device 600 can further include a number of inner reservoirs (inner reservoir 615 is shown), which can include a material with a density less than water and quantum dots. The inner reservoir 615 can be made of a water dissolvable membrane 620, such that when dissolved, empties the inner material and quantum dots into the surrounding water environment. In exemplary embodiments, each of the quantum dots can be configured to be protected from the water environment, and have a density less than that of water thereby allowing the quantum dots to float. For example, the quantum dots can be coated with a thin water insoluble membrane. As such, by having multiple nested reservoirs, the device 600 can release quantum dots over time as each inner reservoir dissolves, thus enabling quantum dots to be dispersed if the aircraft, boat or victim has drifted over time.

In exemplary embodiments, the quantum dots can absorb all ambient light, and emit the light back at a tuned frequency as described herein. In this way, receivers on aircraft or satellites can be tuned to search for those tuned frequencies. In exemplary embodiments, the device can also be actively shined with radiation of the specified frequency to excite the quantum dots to reemit the light waves. In exemplary embodiments, a wave source 450 (e.g., a UV laser) can be implemented to activate the quantum dots in material 630 released by the device 600. A receiver 455 that interprets the wavelengths of the excited beam 658 to determine the presence of dots in material 630. In exemplary embodiments, an incident beam 656 from the wave source 650 can be shined into the material 630, generating an area of excitation 657, resulting in a excited beam signal 658, which is detected by the receiver 455. As described herein, the wave source 450 and receiver 455 can be positioned on various search and rescue vehicles such as aircraft, boats and satellites. In addition, at night, rescuers can shine the wave source 450 on the water and it will light up instead of being absorbed by the water. The brighter the light coming from the water the closer they are to the source (i.e., "the victim").

As such, the systems and methods described herein can reduce search time while increasing search success by making it possible for sensors to scan a large area from a high altitude. The quantum dots can be tuned to emit in frequencies that are not normally emitted by the water's surface. The sensors can be designed to pick up on light frequencies that aren't normally emitted from the water's surface. In addition, since the device 600 described herein is dissolvable, there is no need for a survivor to activate the system.

Figure 7:
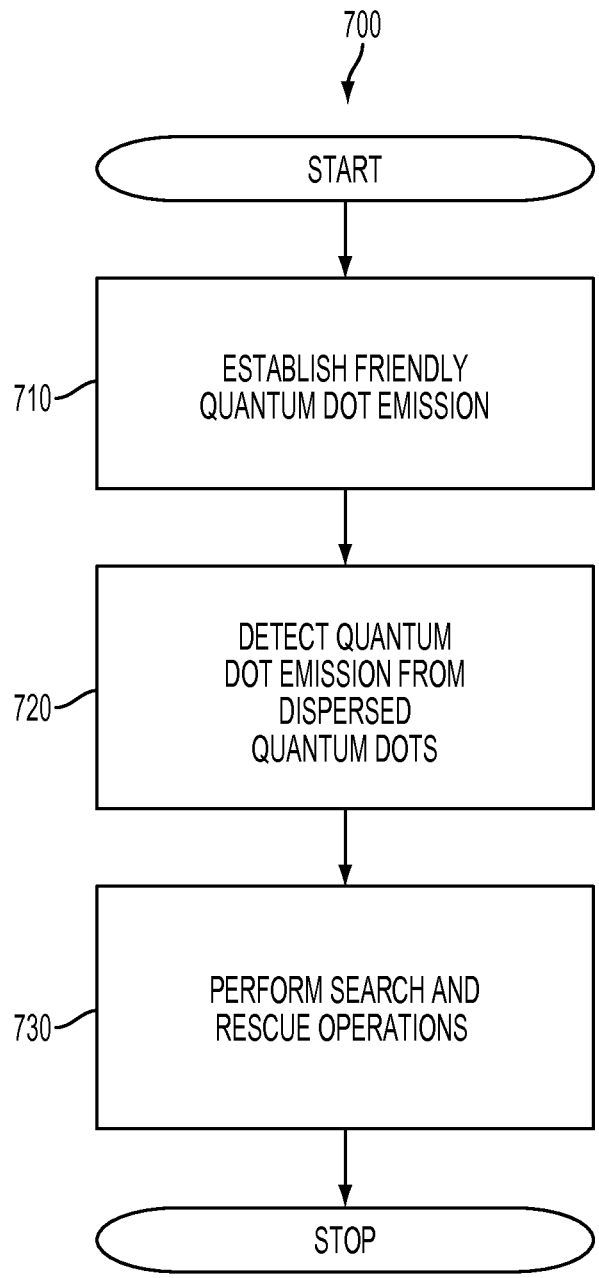
FIG. 7 illustrates a flow chart of a method for locating positions/objects implementing quantum dots in accordance with exemplary embodiments.

FIG. 7 illustrates a flow chart of a method 700 for locating positions/objects implementing quantum dots in accordance with exemplary embodiments. At block 710, a quantum dot emission spectrum is selected for locating positions/objects. As such, a pre-selected emission is known, which, when detected at block 720, upon activation of the device 600 in an aquatic environment. At block 730, search and rescue actions can be implemented.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. An identification system for identifying an article, comprising:
    a strobe disposed on the article that flashes in response to a detection of a light wave query;
    a quantum dot form factor disposed on the article with the strobe underneath the quantum dot form factor relative to a predominant direction of the light wave query; and
    a plurality of quantum dots disposed on the quantum dot form factor, the plurality of quantum dots configured to emit, responsive to strobe flashing, a predetermined emission in a direction that opposes the predominant direction of the light wave query for detection by an external receiver.

2. The system as claimed in claim 1 wherein the light wave query is directed from an external light source.

3. The system as claimed in claim 2 further comprising an external device for detecting the emission and generating a disable communication in response thereto.

4. The system as claimed in claim 3 wherein the disable communication is configured to disable an external weapon system.

5. The system as claimed in claim 1 wherein the plurality of quantum dots emits the predetermined emission in response to an activation from a source of the light wave query.

6. The system as claimed in claim 5 further comprising an external device for generating a disable communication and wherein the disable communication is configured to disable an external weapon system.

7. The system as claimed in claim 1 wherein the light wave query and the emission is light at a predetermined ultraviolet (UV) frequency.

8. A marking system, comprising:
    a reservoir including a plurality of quantum dots configured to be expelled from the reservoir;
    a means for dispersing the quantum dots from the reservoir to engage the area to be marked; and
    an external receiver configured to detect a predetermined emission from at least a portion of the plurality of quantum dots following dispersal and upon activation of the portion of the plurality of quantum dots by a laser.

9. The system as claimed in claim 8 further comprising a dispersible material disposed in the reservoir.

10. The system as claimed in claim 9 wherein the dispersible material is mixed with the plurality of quantum dots.

11. The system as claimed in claim 8 wherein the reservoir comprises main and secondary reservoirs,
    the main reservoir including compressed gas and the secondary reservoir being located within the main reservoir, and
    the marking system further comprising a trigger coupled to the main reservoir and the secondary reservoir.

12. The system as claimed in claim 11 wherein the trigger is configured to release the compressed gas and the plurality of quantum dots into an environment external to the system.

13. The system as claimed in claim 12 further comprising a breakable membrane disposed between the main reservoir and the secondary reservoir.

14. The system as claimed in claim 13 wherein the membrane isolates the compressed gas from the plurality of quantum dots.

15. A location system, comprising:
    a reservoir having a plurality of quantum dots disposed therein,
    the reservoir comprising a water dissolvable material that dissolves over a predetermined period while exposed to water to thereby disperse the plurality of quantum dots into the water; and
    an external receiver configured to detect a predetermined emission from at least a portion of the plurality of quantum dots following dispersal and upon activation of the portion of the plurality of quantum dots by a laser.

16. The system as claimed in claim 15 wherein the reservoir comprises:
    a main reservoir having a plurality of quantum dots disposed therein; and
    an inner reservoir having another plurality of quantum dots disposed therein,
    the main and inner reservoirs respectively comprising water dissolvable materials that respectively dissolve over predetermined periods while exposed to water.

17. The system as claimed in claim 15 wherein the reservoir comprises a plurality of nested reservoirs, each having plurality of quantum dots disposed therein, and each comprising respective water dissolvable materials that dissolves over predetermined periods while exposed to water.

18. An identification system for allowing a person or thing to identify themselves by emitting a coded light frequency in response to a light wave query, the identification system comprising:
    a sensor disposed on a first portion of an article for detecting a light wave query;
    a strobe disposed on a second portion of the article for flashing in response to the detection of a light wave query; and
    a filter at least partially covering said strobe such that the strobe is underneath the filter relative to a predominant direction of the light wave query,
    said filter including quantum dots that the light from the strobe energizes to emit light in a direction that opposes the predominant direction of the light wave query and at a predetermined frequency which is detectable to determine the identity of the person or thing.

19. The identification system as claimed in claim 18 further comprising a power source coupled to the strobe.

20. The identification system as claimed in claim 18, wherein the quantum dots emit at least one of a single and multiple frequency bands.

21. The identification system as claimed in claim 18 wherein the quantum dots are tunable.

22. The identification system as claimed in claim 18 wherein the article is wearable by a person.

23. The identification system as claimed in claim 18 further comprising a receiver configured to detect light emitted through the filter to identify the person or thing.

24. The system as claimed in claim 23 wherein the receiver is configured to trigger a lockout signal to disable a weapon system coupled to the identification system.

* * * * *